United States Patent [19]

Manoury

[11] 4,341,893
[45] Jul. 27, 1982

[54] QUINAZOLINE DERIVATIVES

[75] Inventor: Philippe M. J. Manoury, L'Hay les Roses, France

[73] Assignee: Synthelabo, Paris, France

[21] Appl. No.: 795,375

[22] Filed: May 9, 1977

[30] Foreign Application Priority Data

May 7, 1976 [FR] France ............................... 76 13681
Aug. 24, 1976 [FR] France ............................... 76 25563

[51] Int. Cl.³ .................. C07D 239/95; C07D 401/04; C07D 413/12; C07D 413/14
[52] U.S. Cl. ..................................... 544/284; 544/291
[58] Field of Search ................. 260/256.4 Q; 544/291, 544/284

[56] References Cited

U.S. PATENT DOCUMENTS

| | | | |
|---|---|---|---|
| 3,511,836 | 5/1970 | Hess et al. | 260/256.4 Q |
| 3,635,979 | 1/1972 | Hess | 424/251 |
| 3,663,706 | 5/1972 | Hess | 424/251 |
| 4,001,238 | 1/1977 | Partyka et al. | 260/256.4 Q |

Primary Examiner—Paul M. Coughlan, Jr.

Attorney, Agent, or Firm—Wegner & Bretschneider

[57] ABSTRACT

Quinazoline derivatives of the formula (I):

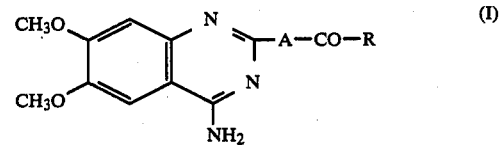

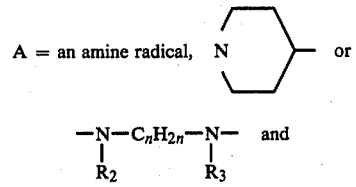

$-N-C_nH_{2n}-N-$ and
$\phantom{-N-}R_2\phantom{C_nH_{2n}-}R_3$

R=phenyl which is optionally substituted, furyl, thienyl or 5-alkylthio-1,3,4-oxadiazol-2-yl. These derivatives are useful as drugs, e.g. anti-hypertensive agents.

7 Claims, No Drawings

QUINAZOLINE DERIVATIVES

The present invention relates to quinazoline derivatives, their preparation and their application in therapy.

U.S. Pat. Nos. 3,511,386, 3,635,979 and 3,663,706 describe various 4-amino-6,7-dimethoxy-2-[4-(heterocyclic radical)-2-carbonyl-piperazin-1-yl]quinazolines. One of these compounds, 2-[4-(2-furoyl)-piperazin-1-yl]-4-amino-6,7-dimethoxy-quinazoline or prazosine, is an anti-hypertensive agent which is available commercially but which however exhibits adverse side-effects.

The present application provides quinazoline derivatives corresponding to the formula (I)

[Structure I: 4-amino-6,7-dimethoxyquinazoline with substituent —A—CO—R at 2-position]

in which: A represents an amine radical,

[Structure: piperidine ring attached via N, or $-N-C_nH_{2n}-N-$ with $R_2$ and $R_3$ substituents]

in which n is 2, 3 or 4 and $R_2$ and $R_3$ each represent, independently of one another, a hydrogen atom or an alkyl radical of 1 to 4 carbon atoms, and R represents a phenyl radical which can carry one or more substituents chosen from amongst alkyl radicals and alkoxy radicals with 1 to 4 carbon atoms, and methylenedioxy, furyl, thienyl, and 5-alkylthio-1,3,4-oxadiazol-2-yl radicals; and their addition salts with pharmaceutically acceptable acids.

These compounds are anti-hypertensive agents which do not exhibit side-effects.

According to the invention, the compounds are prepared: either by condensation of the quinazoline (II)

[Structure II: 4-amino-6,7-dimethoxy-2-X-quinazoline, X = halogen]

with the compound HA—CO—R—(III), or, if A is a $$-N-C_nH_{2n}-N-$$
$$\quad | \qquad\qquad | $$
$$\quad R_2 \qquad\quad R_3$$

radical, by reaction between the quinazoline (IV)

[Structure IV: 4-amino-6,7-dimethoxy-2-(N(R2)-CnH2n-N(R3)-H)-quinazoline]

and an acid chloride RCOCl (V).

The condensation is carried out by heating a mixture of approximately stoichiometric quantities of the two reagents at the reflux temperature of a polar solvent, such as an alcohol, for example isoamyl alcohol. However, it is possible to use a slight excess (up to 15%) of the 2-halogeno-substituted quinazoline and, in certain cases, a trace of sodium iodide can be added as the catalyst. The heating time is from 2 to 10 hours and in general from 2½ hours to 7 hours, depending on the compounds present.

The second reaction is carried out by adding an acid halide, at a temperature of between 0° and 50°, to a solution of IV in a non-polar solvent such as chloroform, in the presence or absence of a hydracid acceptor such as sodium hydroxide, triethylamine or pyridine.

The following examples illustrate the invention.

The IR and NMR spectra, as well as microanalyses, have confirmed the structure of the compounds.

EXAMPLE 1

4-Amino-6,7-dimethoxy-2-[4-(3,4-methylenedioxybenzoyl)piperidino]-quinazoline and its hydrochloride

[A = N-piperidinyl, R = 3,4-methylenedioxyphenyl]

A mixture of 0.950 g (0.004 mol) of 3,4-methylenedioxyphenyl-piperidyl-4 ketone, 0.950 g (0.004 mol) of 4-amino-2-chloro-6,7-dimethoxyquinazoline and 50 ml of isoamyl alcohol is heated under reflux for 5 hours.

A precipitate forms which is filtered off at 30°. This precipitate is recrystallised from a mixture of methylene chloride, methanol and isopropanol. Thereafter the precipitate is washed with ether and dried at 80° C. under reduced pressure. If necessary, the product is recrystallised a second time in the same way.

1.1 g (yield 58%) of 4-amino-6,7-dimethoxy-2-[4-(3,4-methylenedioxybenzoyl)-piperidino]-quinazoline hydrochloride, which melts at more than 270° C., are thus collected.

EXAMPLE 2

4-Amino-6,7-dimethoxy-2-[4-(3-methoxybenzoyl)-piperidino]-quinazoline and its methane-sulphonate

[A = N-piperidinyl; R = 3-methoxyphenyl (OCH₃)]

6.8 g (0.031 mol) of 4-(3-methoxybenzoyl)piperidine and 6.69 g (0.0279 mol) of 4-amino-6,7-dimethoxy-2-chloroquinazoline in 60 ml of isopropyl alcohol are maintained at reflux temperature for one day. Thereafter the precipitate is filtered off, washed with isoamyl alcohol and ether and dried in an oven.

12.3 g of the hydrochloride of the product referred to are obtained.

The base is recovered by reacting the salt with sodium hydroxide in chloroform. After recrystallisation from ether, 4-amino-6,7-dimethoxy-2-[4-(3-methoxybenzoyl)-piperidino]-quinazoline melts at 217° C. (sic).

The methane-sulphonate is prepared by reacting the above base with the acid in a mixture of methanol and ethanol.

This salt melts at 257° C. (instantaneous melting at 216° C. and resolidification and complete melting at 257° C. on a Kofler bench).

EXAMPLE 3

$N_1$-(4-amino-6,7-dimethoxy-quinazolinyl-2)-$N_1$ $N_2$-dimethyl-$N_2$-(furoyl-2)-propylenediamine and its monohydrochloride

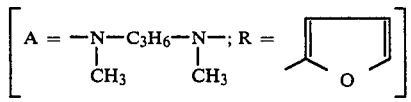

(a)

$N_1$-(4-amino-6,7-dimethoxy-quinazolinyl-2)-$N_2$-benzyl-$N_1N_2$-dimethyl-propylenediamine A mixture of 4.80 g (0.02 mol) of 4-amino-2-chloro-6,7-dimethoxy-quinazoline, 7.7 g (0.04 mol) of $N_1$-benzyl-$N_1N_2$-dimethyl-propylenediamine and 1.6 g (0.02 mol) of pyridine is heated for one hour at 135°–140° C.

After cooling, 200 ml of methylene chloride are added and the residue is filtered off and rinsed with ether. The product is recrystallised twice from isopropyl alcohol containing a little ethanol and hydrochloric acid.

4.6 g (yield 53%) of $N_1$-(4-amino-6,7-dimethoxy-quinazolinyl-2)-$N_2$-benzyl-$N_1N_2$-dimethyl-propylenediamine hydrochloride, which melts at 198° C., are collected.

The base obtained according to the conventional method melts at 128° C.

(b)

$N_1$-(2-amino-6,7-dimethoxy-quinazolinyl-2)-$N_1N_2$-dimethyl-propylenediamine and its dihydrochloride 8 g (0.0176 mol) of $N_1$-(4-amino-6,7-dimethoxy-quinazolinyl-2)-$N_2$-benzyl-$N_1N_2$-dimethyl-propylenediamine monohydrochloride, 250 ml of methanol, 5.2 ml of 3.4 N hydrochloric acid in ethanol and 3 g of 10% strength palladium on charcoal are put into a 500 ml autoclave.

The mixture is hydrogenated under a pressure of 20 kg/cm² at 40° C. The hydrogen absorption is very rapid.

After cooling, the mixture is extracted with 70% strength methanol in water and the catalyst is filtered off. The solvent is evaporated and the residue is taken up twice in suspension in boiling ethanol.

$N_1$-(2-amino-6,7-dimethoxy-quinazolinyl-2)-$N_1N_2$-dimethylpropylenediamine dihydrochloride is collected, which melts at 240° C. (Base melting point=173° C.)

(c)

$N_1$-(4-amino-6,7-dimethoxy-quinazolinyl-2)-$N_1N_2$-dimethyl-$N_2$-(furoyl-2)-propylenediamine and its hydrochloride 3 ml (0.03 mol) of 10 N sodium hydroxide are added to a solution of 5.7 g (0.015 mol) of $N_1$-(2-amino-6,7-dimethoxyquinazolinyl-2)-$N_1N_2$-dimethyl-propylenediamine dihydrochloride in 30 ml of water and 30 ml of methanol. The solvents are evaporated, the residue is suspended in 50 ml of chloroform and 2.1 g (0.016 mol) of furoyl-2 chloride are added. Stirring is carried out for 3 hours at 20° C., then 50 ml of methanol are added and the mixture is left standing overnight.

After evaporation of the solvents, the residue is taken up in chloroform and 5 N sodium hydroxide is added. The aqueous phase is separated off and extracted twice with chloroform. The combined chloroform extracts are dried over magnesium sulphate and then evaporated.

$N_1$-(4-amino-6,7-dimethoxy-quinazolinyl-2)-$N_1N_2$-dimethyl-$N_2$-(furoyl-2)-propylenediamine is thus obtained, which does not crystallise. The compound is converted to its hydrochloride by reacting with hydrochloric acid in solution in ethanol and isopropyl alcohol. The salt obtained is recrystallised from a mixture of ethanol and methylene chloride.

The monohydrochloride is obtained with a yield of 78%. The salt melts at 163° C.

EXAMPLE 4

$N_1$-(4-amino-6,7-dimethoxy-quinazolinyl-2)-$N_2$-benzoyl-$N_1N_2$-dimethyl-propylenediamine and its monohydrochloride

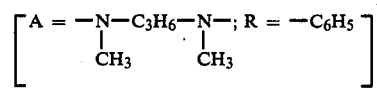

A mixture of 5.9 g (0.0247 mol) of 4-amino-2-chloro-6,7-dimethoxy-quinazoline, 10.2 g (0.0494 mol) of $N_1$-benzoyl-$N_1N_2$-dimethyl-propylenediamine and 150 ml of isoamyl alcohol is heated under reflux for 6 hours in a 250 ml Erlenmeyer flask equipped with an electromagnetic stirrer. The solvent is evaporated to dryness, under reduced pressure, the residue is treated with sodium bicarbonate in solution in water and this solution is treated with chloroform. After several successive treatments with water and with chloroform, the chloroform extract is dried over magnesium sulphate and the solvent is evaporated.

$N_1$-(4-amino-6,7-dimethoxy-quinazolinyl-2)-$N_2$-benzoyl-$N_1N_2$-dimethyl-propylenediamine is thus collected, which is converted into its monohydrochloride.

After two recrystallisations from isopropyl alcohol, 5.8 g of the salt (yield: 52.7%) which melts at 218°–220° C., are obtained.

EXAMPLE 5

$N_1$-(4-amino-6,7-dimethoxy-quinazolinyl-2)-$N_2$-benzoyl-$N_2$-methyl-propylenediamine and its hydrochloride

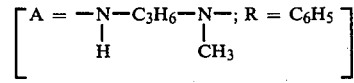

(a) 3-(N-benzoyl-N-methyl-amino)-propionitrile 35.2 g (0.42 mol) of N-methyl-3-amino-propionitrile (prepared as described in J. Chem. Soc. 1945, 399–402) in 100 ml of methylene chloride are added to a solution of 94 g (0.42 mol) of benzoic anhydride in 100 ml of the same solvent. The temperature rises to 50° C. since the reaction is exothermic. After stirring for about 1½ hours, the mixture is treated with an iced solution of sodium hydroxide and then washed with water and the organic phase is dried over $Na_2SO_4$. The solvent is evaporated under reduced pressure. 68 g of nitrile (yield 87%) are obtained. Boiling point=140° C./0.06 mm of Hg.

(b) N-benzoyl-N-methyl-propylenediamine 15.1 g (0.08 mol) of the above nitrile in 40 ml of methanol are placed in a 125 ml container which withstands pressure. The solution is saturated cold with ammonia and hydrogenated at 100° under an initial hydrogen pressure of 80 atmospheres, using a Raney nickel catalyst. When the hydrogen absorption is finished, the catalyst is filtered off and the mixture is washed with alcohol. The reaction product is fractionated in vacuo. The expected amide boils at 155°–158° C./0.1 mm of Hg. 5.8 g (yield 38%) of the product are collected. This compound gives a hydrochloride which melts at 102° C.

(c) $N_1$-(4-amino-6,7-dimethoxy-quinazolinyl-2)-$N_2$-benzoyl-$N_2$-methyl-propylenediamine 5.6 g (0.029 mol) of the above amide and 6.25 g (0.026 mol) of 4-amino-2-chloro-6,7-dimethoxy-quinazoline in 50 ml of isoamyl alcohol are heated at the reflux temperature for 4 hours. After standing overnight, 9.9 g of $N_1$-(4-amino-6,7-dimethoxy-quinazolinyl-2)-$N_2$-benzoyl-$N_2$-methylpropylenediamine hydrochloride are filtered off and recrystallised from absolute ethanol. The salt melts at 168.2° C.

The base is obtained by reacting the hydrochloride with sodium hydroxide in chloroform, drying the solution over $Na_2SO_4$ and evaporating the solvent under reduced pressure.

The base melts at 171° C.

EXAMPLE 6

4-amino-6,7-dimethoxy-2-[4-(5-methylthio-1,3,4-oxadiazole-2-carbonyl)-piperidino]-quinazoline

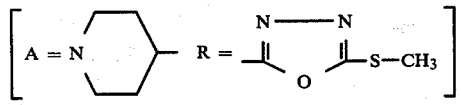

2.13 g of 4-(5-methylthio-1,3,4-oxadiazole-2-carbonyl)-piperidine and 2.4 g of 2-chloro-4-amino-6,7-dimethoxy-quinazoline in 50 cm³ of isoamyl alcohol are heated under reflux for 8 hours with stirring. After cooling and concentration, 3.9 g of product are isolated, which are purified by recrystallisation from ethanol.

3.1 g of hydrochloride are obtained, namely a yield of 68%; melting point <270° C.

EXAMPLE 7

$N_1$-[4-amino-6,7-dimethoxy-quinazolinyl-2]-$N_2$-[(5-methylthio-1,3,4-oxadiazole-2-carbonyl]-$N_1N_2$-dimethyl-propylenediamine

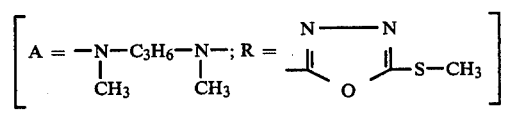

1.8 g of 5-methylthio-1,3,4-oxadiazole-2-carbonyl chloride in solution in 10 cm³ of chloroform are added to a solution of 3.05 g of $N_1N_2$-dimethyl-(4-amino-6,7-dimethoxyquinazolinyl-2)-propylenediamine in 30 cm³ of chloroform. The mixture is stirred at 0° for 1 hour and the reaction is completed by slight heating at 50°. After cooling, the solution obtained is stirred with water containing a bicarbonate. The organic layer is decanted and dried. After evaporation the residue is taken up in isopropanol and hydrogen chloride gas is passed into the solution.

2.9 g of the monohydrochloride are obtained, namely a yield of 60%, after purification by recrystallisation from ethanol; melting point 168° C. The base melts at 136° C.

TABLE I

| COMPOUND | A | R | CHARACTERISTICS | Melting Point (°C.) |
|---|---|---|---|---|
| 1 (Ex 1) | —N(piperidine) | phenyl-O-CH₂-O (methylenedioxyphenyl) | HCl | >270 |
| 2 | —N(piperidine) | phenyl | HCl / base | >270 / 182 |
| 3 (Ex 2) | —N(piperidine) | phenyl-OCH₃ | m s / base | 257 / 217 |
| 4 | —N(piperidine) | phenyl-OCH₃ | HCl | 250–255 |

TABLE I-continued

| COMPOUND | A | R | CHARACTERISTICS | Melting Point (°C.) |
|---|---|---|---|---|
| 5 | -N(piperidine)- | 2-OCH₃-phenyl | m s | 266 |
| 6 | -N(piperidine)- | thiophene | HCl | 285 |
| 7 (Ex 6) | -N(piperidine)- | 1,3,4-oxadiazole-S-CH₃ | HCl | >270 |
| 8 (Ex 3) | -N(CH₃)-C₃H₆-N(CH₃)- | furan | HCl | 163 |
| 9 | -N(CH₃)-C₂H₄-N(CH₃)- | furan | HCl | 262 |
| 10 (Ex 4) | -N(CH₃)-C₃H₆-N(CH₃)- | phenyl | HCl | 218-220 |
| 11 | -N(CH₃)-C₂H₄-N(CH₃)- | phenyl | oxalate | 220 |
| 12 (Ex 5) | -N(H)-C₃H₆-N(CH₃)- | phenyl | base / HCl | 171 / 168.2 |
| 13 | -N(CH₃)-C₃H₆-N(C₂H₅)- | furan | HCl | 210 |
| 14 | -N(CH₃)-C₃H₆-N(CH₂CH(CH₃)CH₃)- | phenyl | HCl | 206 |
| 15 | -N(C₂H₅)-C₃H₆-N(C₂H₅)- | phenyl | HCl | 225 |
| 16 | -N(CH₃)-C₃H₆-N(H)- | phenyl | HCl | 170 |
| 17 | -N(C₂H₅)-C₃H₆-N(CH₃)- | phenyl | HCl | 170 |
| 18 | -N(C₂H₅)-C₃H₆-N(C₂H₅)- | furan | HCl | 166 |
| 19 | -N(H)-C₃H₆-N(H)- | phenyl | base / HCl | 176 / 270 |
| 20 | -N(CH₃)-C₄H₈-N(CH₃)- | phenyl | HCl | 256 |
| 21 | -N(CH₃)-C₃H₆-N(CH₃)- | 3-CH₃-phenyl | HCl | 163 |

TABLE I-continued

| COMPOUND | A | R | CHARACTERISTICS | Melting Point (°C.) |
|---|---|---|---|---|
| 22 | —N(CH₃)—C₃H₆—N(CH₃)— | -C₆H₄-OCH₃ (ortho) | HCl | 191 |
| 23 | —N(CH₃)—C₃H₆—N(CH₃)— | -C₆H₃(OCH₃)₂ (3,5) | HCl | 166 |
| 24 | —N(CH₃)—C₃H₆—N(CH₃)— | -C₆H₂(OCH₃)₃ (3,4,5) | HCl | 178 |
| 25 (Ex 7) | —N(CH₃)—C₃H₆—N(CH₃)— | 5-methylthio-1,3,4-oxadiazol-2-yl | base / HCl | 136 / 168 |

HCl = hydrochloride
m s = methanesulphonate

The compounds of the invention have been subjected to a series of pharmacological tests which have revealed their valuable anti-hypertensive properties.

Acute toxicity

The tests were carried out on CD 1 mice weighing, on average, 20 g.

The compounds were administered orally and the 50% lethal dose (LD 50) was calculated graphically.

The compounds of the invention showed themselves to have low toxicity.

The LD 50 values are greater than 500 mg/kg for the majority of the products.

Anti-hypertensive effect

Experiments were carried out on spontaneously hypertensive male rats (Okamoto strain), which were at least 14 weeks old. The systolic pressure was measured according to the technique described by Gerold and Tschirky (Arzneim.-Forsch. 1968, 18, 1285). The compounds were administered orally at a dose of 1 or 10 mg/kg.

Table II collects together the results obtained which are expressed in percent variation of the initial pressure, 2 hours, 4 hours and 24 hours after administration of the compound (I).

TABLE II

| Compound No. | LD 50 rat mg/kg | Dose perorally mg/kg | 2 hours | 4 hours | 24 hours |
|---|---|---|---|---|---|
| 1 | >500 (ip) | 10 | −30 | −32 | −37 |
| 2 | >500 (ip) | 10 | −43 | −32 | −40 |
| 3 | ≃500 (intraperitoneally) | 10 | −32 | −23 | — |
| 6 | >500 (intraperitoneally) | 10 | −27 | −22 | −2 |
| 7 | >500 (perorally) | 10 | −24 | −20 | −2 |
| 10 | >500 (perorally) | 10 | −23 | −15 | −4 |
| 12 | ≃400 (intraperitoneally) | 10 | −31 | −23 | — |

TABLE II-continued

| Compound No. | LD 50 rat mg/kg | Dose perorally mg/kg | 2 hours | 4 hours | 24 hours |
|---|---|---|---|---|---|

The compounds of the invention therefore exhibit a marked anti-hypertensive activity which is in general very prolonged. Furthermore, they have the advantage of not noticeably modifying the heart beat at doses which are active on hypertension. The therapeutic range is thus large, given their low toxicity.

The results described show that the compounds of the invention are medicines which can be used in human and veterinary therapy, especially in the treatment of all forms of idiopathic or secondary hypertension.

Consequently, the invention comprises all pharmaceutical compositions containing the compounds (I) as the active principles, in association with all excipients suitable for their administration, in particular orally, endorectally or parenterally. These pharmaceutical compositions can also contain other medicinal substances with which the compounds (I) are pharmacologically and therapeutically compatible.

The daily dosage can range from 1 to 400 mg.

We claim:

1. 4-Amino-6,7-dimethoxy-2-[4-(3,4-methylenedioxybenzoyl)-piperidino]-quinazoline and its pharmaceutically acceptable acid addition salts.

2. 4-Amino-6,7-dimethoxy-2-[4-(3-methoxybenzoyl)-piperidino]-quinazoline and its pharmaceutically acceptable acid addition salts.

3. $N_1$-(4-amino-6,7-dimethoxyquinazolinyl-2)-$N_1N_2$-dimethyl-$N_2$-(furoyl-2)-propylenediamine and its pharmaceutically acceptable acid addition salts.

4. $N_1$-(4-amino-6,7-dimethoxyquinazolinyl-2)-$N_2$-benzoyl-$N_1N_2$-dimethylpropylenediamine and its pharmaceutically acceptable acid addition salts.

5. $N_1$-(4-amino-6,7-dimethoxyquinazolinyl-2)-$N_2$-benzoyl-$N_2$-methylpropylenediamine and its pharmaceutically acceptable acid addition salts.

6. 4-Amino-6,7-dimethoxy-2-[4-(5-methylthio-1,3,4-oxadiazole-2-carbonyl)-piperidino]-quinazoline and its pharmaceutically acceptable acid addition salts.

7. $N_1$-[4-amino-6,7-dimethoxyquinazolinyl-2]-$N_2$-[5-methylthio-1,3,4-oxadiazole-2-carbonyl]-$N_1N_2$-dimethylpropylenediamine and its pharmaceutically acceptable acid addition salts.

* * * * *